United States Patent [19]

Krumdieck

[11] Patent Number: 5,522,294

[45] Date of Patent: Jun. 4, 1996

[54] BIOLOGICAL TISSUE SLICER

[76] Inventor: Carlos Krumdieck, 3408 Wellford Cir., Birmingham, Ala. 35216

[21] Appl. No.: 218,420

[22] Filed: Mar. 28, 1994

[51] Int. Cl.$^6$ .................................................. B26D 1/10
[52] U.S. Cl. ...................... 83/411.1; 83/411.4; 83/915.5; 83/468.7
[58] Field of Search ............................. 83/411.4, 411.1, 83/98, 703, 915.5, 169, 468.7, 703, 607, 608; 30/123.3

[56] References Cited

U.S. PATENT DOCUMENTS

| | | | |
|---|---|---|---|
| 2,747,330 | 5/1956 | Simpkins | 30/123.3 |
| 4,492,139 | 1/1985 | Forsstrom et al. | 83/915.5 |
| 4,752,347 | 6/1988 | Rada | 83/915.5 |
| 4,783,907 | 11/1988 | Ravaux | 30/123.3 |
| 5,065,652 | 11/1991 | Legler et al. | 83/169 |
| 5,148,729 | 9/1992 | Krumdieck | 83/411.4 |
| 5,226,335 | 7/1993 | Sitte et al. | 83/703 |

Primary Examiner—Rinaldi I. Rada
Assistant Examiner—Allan M. Schrock
Attorney, Agent, or Firm—Veal & Marsh

[57] ABSTRACT

A tissue slicer having a reciprocating tissue holding blade. A mechanically activated pumping system for flushing liquid medium past a cutting blade into a collection trap. The cutting blade is moved by a reciprocation drive system adjacent and above the cutting blade. The entire slicing assembly is fully autoclavable.

20 Claims, 5 Drawing Sheets

BIOLOGICAL TISSUE SLICER

FIELD OF THE INVENTION

This invention relates to an improved biological tissue slicer designed to produce aseptic thin slices of tissue suitable for biochemical, pharmacological or toxicological studies. The present invention produces uniform tissue slices of a defined thickness with minimal damage at the cut surface. The present invention includes a slicer that operates submerged in a tissue culture media or in a buffer fluid. Further, the invention relates to improvements comprising a mechanical pump and an overhead external drive system for reciprocating a blade and blade holder.

BACKGROUND OF THE INVENTION

Tissue culture methodologies allow physiological reactions and occurrences to be studied outside the organism without the influence of other biological reactions.

Incubation of tissue slices for short periods (hours) was introduced for biomedical studies in 1923 by Warburg. Prolonged incubations (days/weeks) were in practice, not possible until the 1950's, following the introduction of antibacterial and antifungal antibiotics.

There must be uniformity between each individual tissue sample for uniformity and reproducibility among experiments for a tissue culture methodology to be effective. In the past, the production of homogeneous tissue slices from fresh tissue samples has been difficult and dependent on the skill and the experience of the technician. Attempts to produce tissue samples which are uniform in dimension have been met with problems including irreproducibility of slice thickness, contamination of tissue samples and irregular, nonreproducible trauma to the tissue adjacent to the cutting surface.

In U.S. Pat. No. 5,148,729, the applicant disclosed a biological tissue slicer which allowed an inexperienced technician to produce nearly identical tissue slices in an aseptic environment while minimizing tissue trauma. The invention included a blade held in a blade holder between two pins while one or more permanent magnets provide a constant downward pull on the blade and blade holder. The design eliminated need for readjustment or tightening which are opportunities for contamination. The reproducibility of tissue slices is increased as vertical "chatter" of the blade decreases. Also, the exposure of the tissue sample to the blade is limited to reduce the extent of trauma to the cut surface of the tissue.

The Krumdieck device has some disadvantages which do not facilitate the most effective means of slicing tissue. The pumping and trap system of the Krumdieck device complicates the design of the tissue slicer and makes manufacturing the machine more complicated thereby increasing production costs. Krumdieck uses an electric motor mounted in the base to drive a reciprocating blade holder. The motor drives an eccentric pin to convert the rotation of the drive shaft to linear motion in the blade holder. The base mounted motor requires a sealed shaft which extends upward into the buffer reservoir. The seals not only increase production cost but prevent the slicer assembly from being fully autoclavable. The ability to autoclave the entire slicer assembly is crucial to minimize contamination of the tissue samples. Contaminated samples lead to erroneous or unusable information which hampers important and costly research. A simple autoclavable tissue slicer apparatus with a mechanical wash stream pump which is simple and inexpensive to manufacture is needed for biological tissue sampling in the biochemical, pharmacological or toxicological sciences.

SUMMARY OF THE INVENTION

It is an object of this invention to provide a mechanical tissue slicer which rapidly produces aseptic slices of living tissue of nearly identical dimensions while minimizing trauma and contamination to the tissue.

Another object of this invention is to provide a reciprocating drive system for a blade holder and blade which is adjustable and quiet while producing desirable tissue slices.

Still another object of this invention is to provide a mechanical tissue slicer which has a fully autoclavable slicing mechanism.

Yet another object of this invention is to provide a mechanical tissue slicer which is simple and inexpensive to fabricate.

These and other objects of this invention are accomplished through the use of an improved tissue slicer with reciprocating tissue slicer block having a mechanically activated pumping means for flushing liquid medium past the cutting blade into a collection trap. The forced liquid medium carries a freshly sliced tissue sample into the trap with each stroke of the reciprocating block. An external system for driving the reciprocating blade holder utilizes a motor located adjacent to and above the blade and blade holder thereby providing a slicer assembly which can be fully sterilized in an autoclave.

BRIEF DESCRIPTION OF THE DRAWINGS

Apparatus embodying features of the present invention are depicted in the accompanying drawings which form a portion of this disclosure and wherein.

DESCRIPTION OF THE PREFERRED EMBODIMENT

Figure 1:
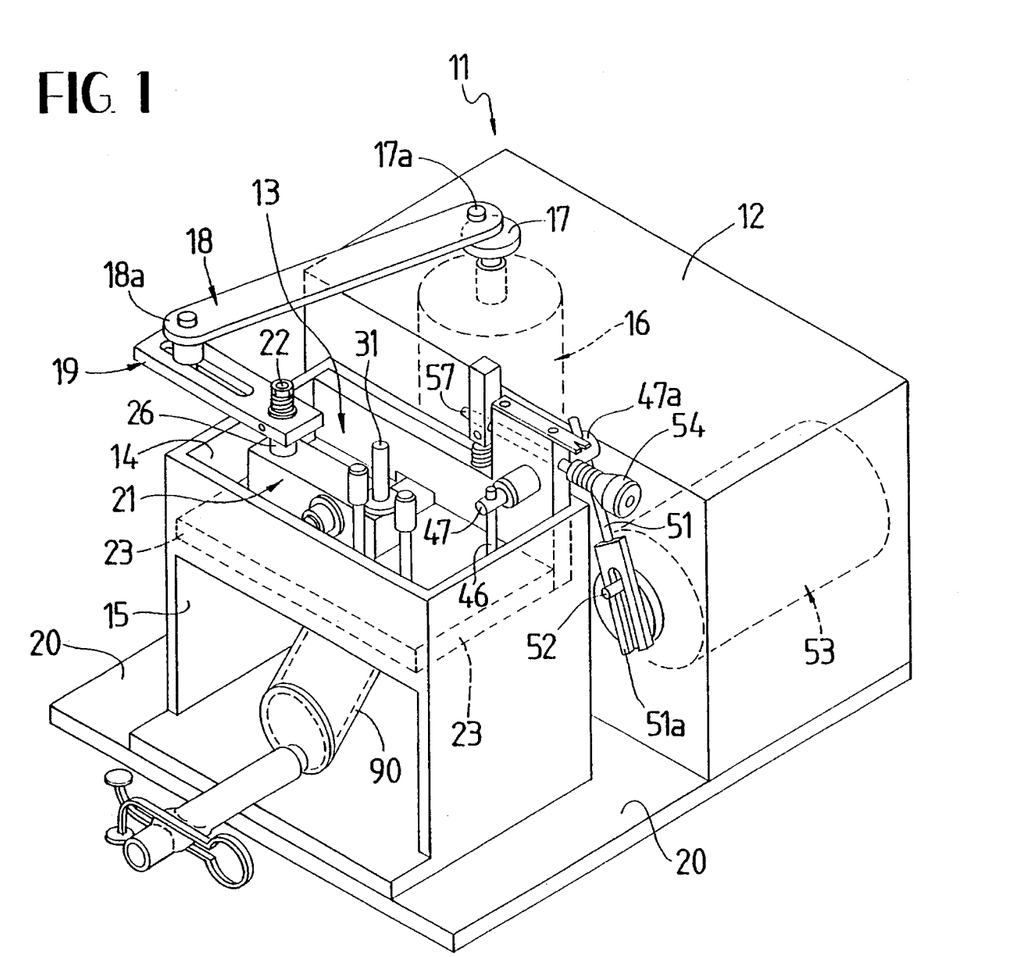
FIG. 1 is a perspective view of the improved tissue slicer.

Referring to the drawings for a clearer understanding of the invention, in FIG. 1 an improved tissue slicer 11 is shown. The slicer 11 primarily consists of a housing 12, a microtome 13, a buffer reservoir 14 containing a quantity of liquid culture medium or buffer fluid and a collection tube 90 supported on a reservoir frame 15. Housing 12 is generally rectilinear and rests on a mounting plate 20 which extends forwardly beneath frame 15. The microtome 13 is mounted superjacent the collection tube 90, and is operated by a pair of electric motors 16 and 53 which are located within housing 12. A first electric motor 16 has a drive wheel 17 which carries an eccentric pin 17a and engages a reciprocating arm 18 pivotally mounted at an end 18a to a lever arm 19 connected to a microtome sample carrier 21.

Figure 2:
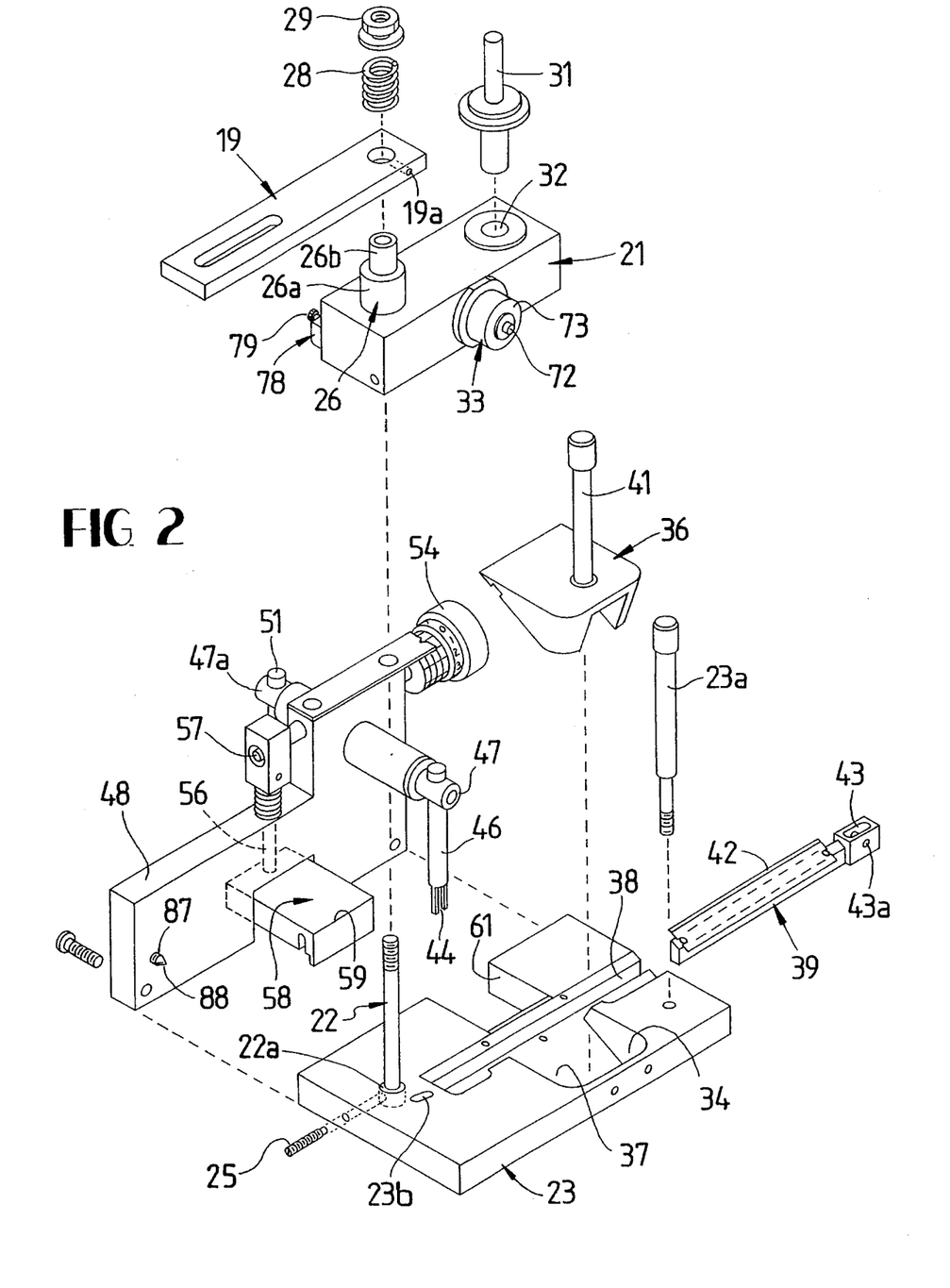
FIG. 2 is an exploded perspective view of the improved tissue slicer.
Figure 3:
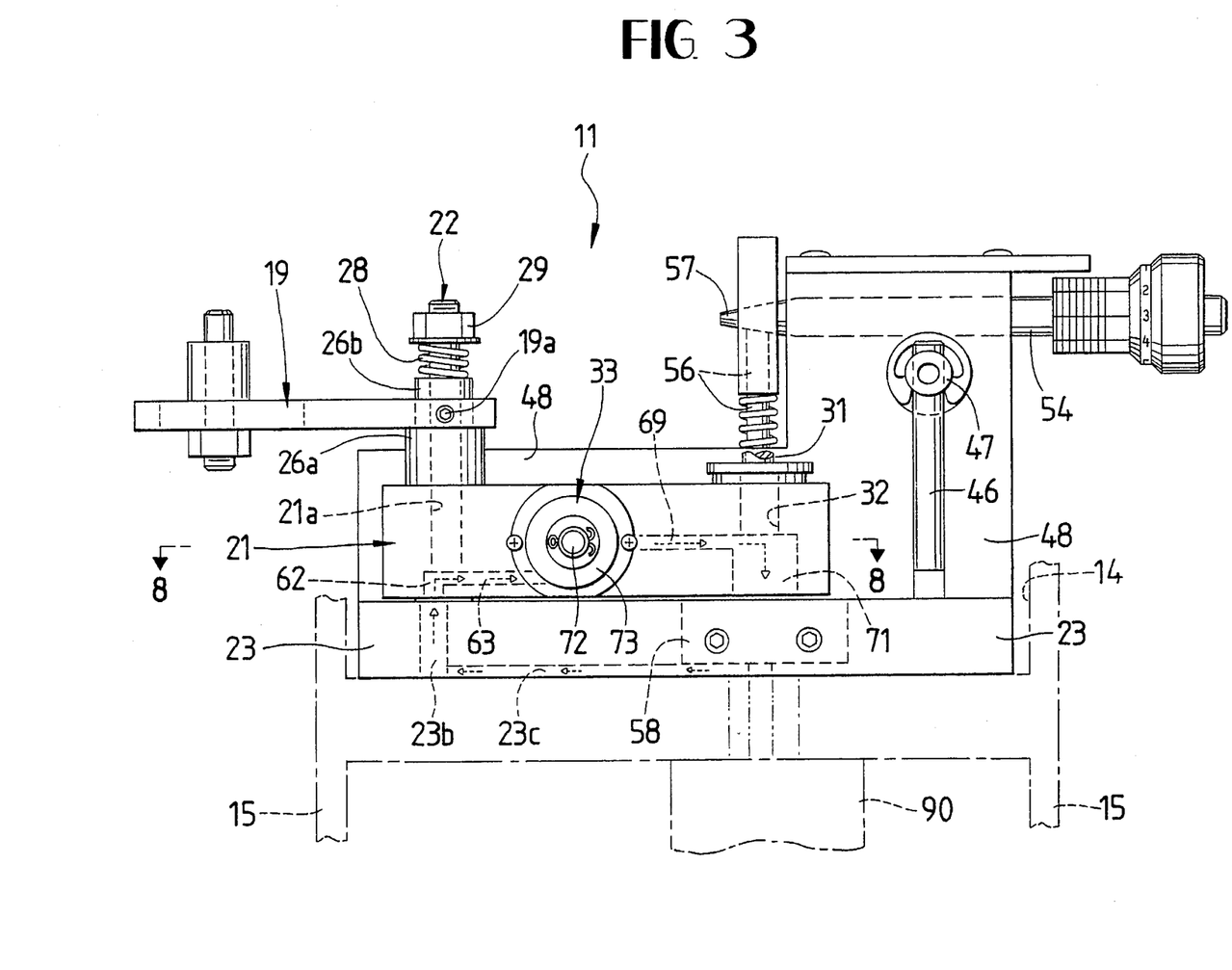
FIG. 3 is front elevational view.
Figure 4:
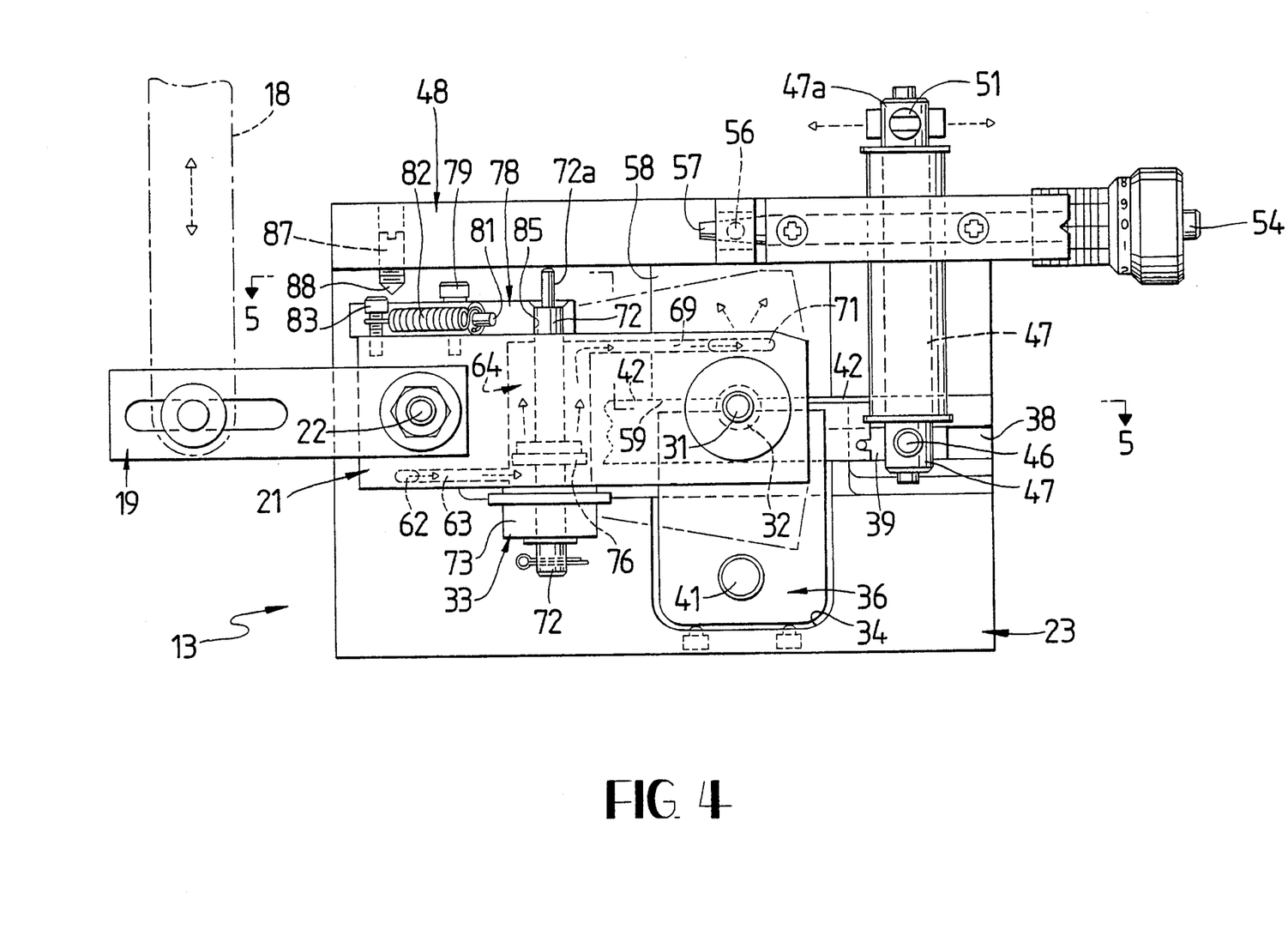
FIG. 4 is a top plan view.

Referring to FIGS. 2–4, tissue carrier 21 is part of the microtome 13 which is mounted within reservoir or medium chamber 14, at least partially submerged in the fluid therein and supported on frame 15 atop mounting plate 20. A base plate 23 is secured in frame 15 by bolts 23a which pass through base 23 and into frame 15. Extending upwardly from base plate 23 is an adjustable pin 22 which is threaded at upper portion and lower portion thereof. Pin 22 has an enlarged diameter portion adjacent the lower threads forming a shoulder 22a. A set screw 25 secures the pin at a desired height within base plate 23. Tissue carrier 21 has a vertical aperture 21a therethrough proximal one end thereof, such that the pin 22 may be inserted therethrough when the carrier 21 is placed in cooperative position relative to base plate 23. The carrier rests on shoulder 22a of pin 22. A sleeve 26 extends upwardly from carrier 21 and circumscribes pin 22.

The sleeve 26 is rigidly affixed to carrier 21 and has a lower major diameter 26a and an upper minor diameter 26b. Minor diameter 26b receives thereon lever arm 19 which is affixed thereto by set screw 19a and is connected at its free end to reciprocating arm 18. A spring 28 is mounted coaxially with pin 22 atop sleeve 26 and is held in position by a nut 29. Thus, as motor 16 rotates the carrier 21 is subjected to oscillation about pin 22 through the linkage of arms 18 and 19.

The tissue carrier 21 receives a weighted plunger 31 in a tissue well 32 defined in block 21. A mechanical pump 33 is transversely mounted within block 21 and flushes liquid medium through block 21.

Referring to FIGS. 3 and 4, the mechanical pump 33 of tissue carrier 21 can be more clearly understood. The tissue carrier 21 pivots about pin 22 on the base plate 23, carrying tissue well 32 over the blade of a slicer in plate 23. Tissue carrier 21 pivots about pin 22 at the urging of motor 16 through the linkage of arms 18 and 19, thus the end of carrier 21 defining tissue well 32 moves in an arc toward and away from back wall 48. As this end moves toward the wall the tissue sample in well 32 is unaffected by the hereinafter described slicing mechanism, however as the well carries the tissue sample away from the wall the intended slicing occurs. Well 32 is located distal pin 22, mechanical fluid pump 33 is located in carrier 21 intermediate well 32 and pivot pin 22. A first opening 62 in the bottom surface of carrier 21 near aperture 21a is in communication with a conduit 63 which extends horizontally within carrier 21 to a cylindrical chamber 64 as best seen in FIG. 3 or 4. The cylindrical chamber 64 extends transversely through carrier 21 having a major diameter opening 67 opposite back wall 48 and a minor diameter aperture 68 adjacent the back wall 48. A second conduit 69 is in communication with chamber 64 and extends horizontally through carrier 21 and connects with a second opening 71 in the lower surface 21b proximal well 32.

Cylindrical chamber 64 has extending therethrough a piston rod 72. The rod is slidably supported by a head mount 73 which sealing engages the major diameter opening 67 and by a minor diameter opening 68. A horizontal pin extension 72a of rod 72 extends a small distance beyond cylindrical minor diameter aperture 68. Coaxially mounted on piston rod 72 is cylindrical piston 76 of a diameter slightly less than the circumference of cylindrical chamber 64 such that the piston does not engage walls 65 of chamber 64. A resilient member 77 such as a helical spring mounts about piston rod 72 between piston 76 and head mount 73. The pin extension 72a engages back wall 48 as the tissue carrier 21 is urged about pin 22 toward the wall 48 thereby urging piston rod 72 and piston 76 against resilient member 77. As may be seen fluid in reservoir 14 will enter chamber 64 through conduit 69 as the piston 76 is urged away from the small diameter end 68 of chamber 64.

Figure 5:
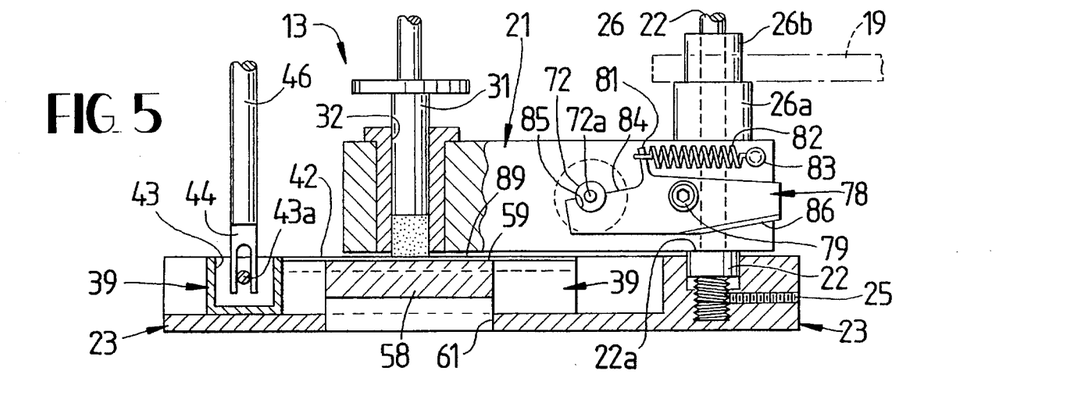
FIG. 5 is a sectional view taken along lines 5—5 of FIG. 4.
Figure 6:
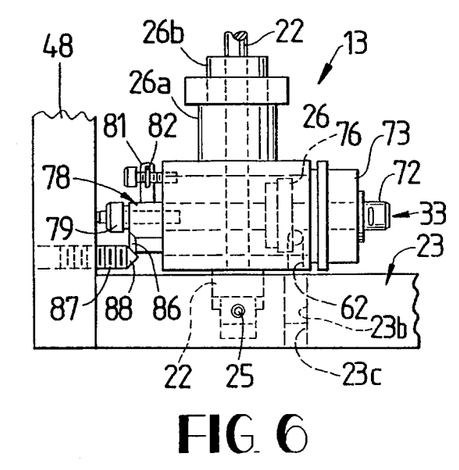
FIG. 6 is a side elevational view as seen from the left side of FIG. 3.
Figure 7:
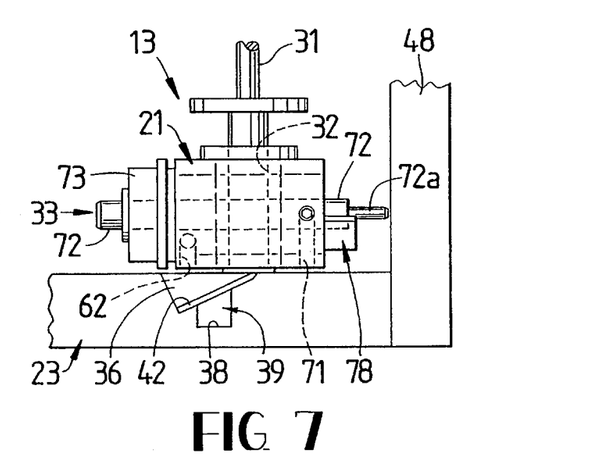
FIG. 7 is a side elevational view as seen from the right side of FIG. 3.
Figure 8:
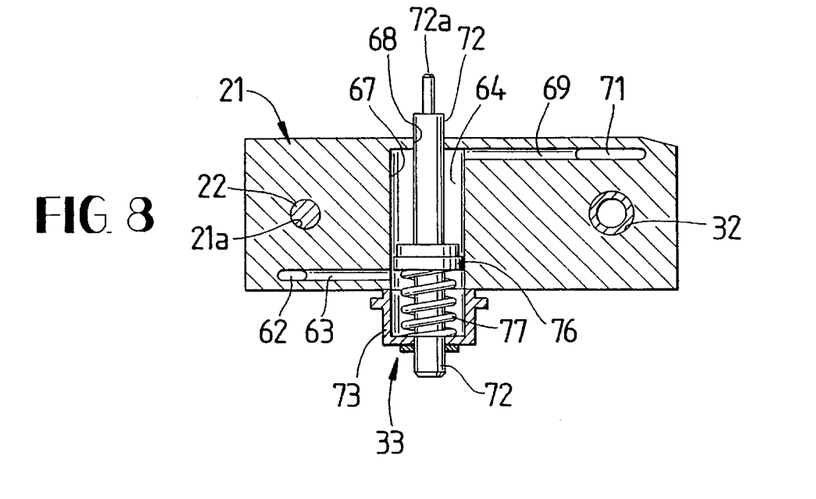
FIG. 8 is a sectional view of the sample carrier taken along lines 8—8 of FIG.3.

Mounted to tissue carrier 21 adjacent the back wall 48 is a trigger member 78 which pivots about a pin 79 which extends normally to carrier 21 as indicated in FIGS. 5 and 6. The trigger 78 includes a upwardly extending prong 81 which is affixed at one end of a horizontal spring 82 which fastens at an opposite end to a screw 83 extending from tissue carrier 21. The trigger 78 has an upper edge 84 which defines an arcuate surface 85 which engages the piston rod 72 as may be seen in FIG's 4 to 7. Horizontal spring 82 biases the arcuate surface 85 upwardly such that the piston rod 72 is frictionally engaged thereby. As carrier 21 pivots toward back wall 48, rod extension 72a engages the back wall such that piston rod 72 and piston 76 are urged against resilient member 77 until the arcuate surface 85 engages the pin extension 72a thereby retaining the piston rod 72 and piston against the resilient member 77 as is best shown in FIGS. 4 and 6.

The trigger member 78 defines an inclined lower surface 86 beneath pin 83 as seen in FIG. 5. A horizontal trip pin 87 extends perpendicularly from back wall 48 such that a conical end 88 of pin 87 is fixedly mounted proximal trigger member 78. As carrier 21 pivots clockwise as shown in FIG. 4, to complete the hereinafter described slicing of the tissue sample, end 88 acts like a cam on the surface 86 of trigger 78 thereby pivoting the trigger member 78 about the pivot point of fastener 79 to disengage the arcuate surface 85 from pin extension 72. Thus, the resilient member 77 expulsively urges the piston rod 72 and piston 76 towards the minor diameter opening 68 of chamber 64.

It will be appreciated that opening 62 is positioned proximal a slot 23b in base plate 23 such that it remains in fluid communication with collection tube 90. A channel 23c extends along a lower surface of base plate 23 as shown in FIGS. 3 and 6. Channel 23c aspirates fluid through an aligned orafice from the collection tube 90 of the reservoir at the instant fluid is discharged. Thus, as carrier 21 is rotatably moving well 32 toward wall 48, piston 76, piston rod 72 and pin 72a engage the wall 48 and move piston 76 away from the wall 48 compressing spring 77. Excess fluid behind the piston 76 is returned to the reservoir and collection tube 90 through conduits 62, 63, 23b, 23c and some fluid passes around the piston 76 into chamber 64. Likewise, fluid is aspirated into the chamber through conduit 69. When pin 87 cams trigger 78 to release rod 72, piston 76 is urged rapidly toward minor diameter 68 and conduit 69, thereby forcefully ejecting fluid through portal 71 and drawing equal amounts of fluid within chamber 64 through conduit 23c.

Referring now to FIG. 2, the base 23 has a slicer wedge cavity 34 defined therein to receive a slicer wedge 36 and align the top surface of the wedge 36 with the top surface of base 23. The wedge 36 is held within the cavity 34 by a threaded member 41 which extends through the wedge 36 and engages the base 23. The cavity 34 has a first inclined surface 37 having a rectangular groove 38 formed therein for receiving a blade holder 39. A blade 42 rests within the blade holder 39 as discussed in detail in the applicants previous Pat. No. 5,148,729. The blade holder 39 is slidingly received in the groove 38 and has a receiving slot 43 defined on one thereof for engaging a pair of depending forks 44 of a reciprocating drive arm 46 as shown in FIG. 5.

The drive arm 46 connects to the end of a shaft 47 which is rotatably mounted and extends perpendicularly through a back plate 48. Opposite end 47a of shaft 47 connects to a drive arm 51 which carries a fork 51a which receives therein an eccentric drive pin 52 which is rotated by a second electric motor 53 as best seen in FIGS. 1 and 2. As may be comprehended in FIGS. 1 and 2, as pin 52 moves within fork 51a, the rotational motion of the pin is converted into oscillating motion of the arm 51, shaft 47 and arm 46. Fork 44 captures pin 43a of blade holder 37 and urges the blade holder in reciprocal motion within groove 38. Thus, as carrier 21 oscillates about pin 22, the tissue in well 32 is sliced by blade 42 as in my prior patent. As the carrier 21 moves the tissue well beyond the blade 42, it brings port 71 proximal the blade 42, whereupon, trigger 78 is actuated to discharge the fluid from chamber 64 through conduit 69 and port 71 and a gap 89 and effectively flush the tissue sample beneath the slicer into the collection tube 90.

The back plate 48 carries therein a horizontally disposed rotatably mounted screw adjustment rod 54. The screw adjustment rod 54 has a conical end 57 which rests atop a rod-like member 56 which is vertically mounted in back plate 48. Rotation of the screw adjustment rod-like rod 54 varies the engagement of conical end 57 with the rod-like member 56 causing the rod-like member to move vertically then to move a slicer plate 58. The vertically movable slicer plate 58 is received within a square channel opening 61 defined by base 23. A reference edge 59 of plate 58 rests adjacent blade 42. A gap 89 beneath blade 42 and edge 59 is in communication via an orifice with a collection tube 90. Thus, the blade 42 remains a predetermined height and the slicer plate 58 is moved relative blade 42 to vary slice thickness.

To operate the slicer 11, the tissue sample is placed within the tissue well 32 and the plunger 31 is replaced atop the tissue sample. Next, the first and second motors 16, 53 are initiated which move the slicer block 21 about rod 22 and induce reciprocal movement of the blade holder 39 and blade 42. As the slicer block 21 reciprocates the back wall 48 engages pin extension 72a and urges the piston rod 72 and piston 76 towards an end of chamber 64 opposite the wall 48 and against resilient member 77. The arcuate surface 85 of trigger member 78 then retains the piston rod 72 in this position. Further reciprocal movement of carrier block 21 forces the conical end 88 of pin 87 to engage the inclined lower surface 86 of trigger member 78 which forces the arcuate surface 85 to disengage from pin extension 72a allowing for the resilient member to quickly urge the piston 76 and piston rod 72 toward the minor diameter of chamber 64 forcing liquid medium through conduit 69 and out second opening 71. The liquid medium carries a freshly cut tissue sample underneath blade 42 to a gap 89 located between surface edge 59 of adjustable plate 58 and out to collection tube 90 in communication with said gap 89 below the medium chamber 14 as seen in FIG. 1. The speed of the second motor can be varied to regulate the rate at which tissue samples are cut by blade 42. Note that the microtome 13, carrier 21, and base plate 23 can all be removed from the buffer reservoir 14 and placed in an autoclave or other sterilization equipment whereas the housing and motors are independently mounted and thus do not require simultaneous autoclaving as did the prior art. It will also be appreciated that the invention lends itself to variations, such as displacement of the blade reciprocation by merely varying the height of motor 53 and the length of drive fork 51.

While I have shown my invention in one form, it will be obvious to one skilled in the pertinent art that it is not so limited, but is susceptible to various changes and modifications without departing from the spirit thereof.

What I claim is:

1. In a tissue slicer for use in preparing tissue samples for medical research, including a base plate, a reciprocally movable blade assembly mounted thereon, a variable height reference plate adjacent said blade assembly defining an opening through said base plate intermediate said blade assembly and said reference plate, and a tissue carrier cooperatively positioned to move a block of tissue relative to said blade assembly and said reference plate to create a slice of tissue having a predetermined thickness, all mounted within a reservoir containing a buffer medium, the improvement comprising:

(a) means mounted externally of an separable from said reservoir for reciprocally driving said blade assembly detachably connected thereto by a drive linkage extending above said buffer medium and externally of said reservoir and, (b) means mounted externally of and separable from said reservoir for iteratively urging said tissue carrier transversely of said blade assembly, detachably connected thereto by a reciprocating linkage extending above said medium and externally of said reservoir.

2. In a tissue slicer as defined in claim 1, means for positioning said tissue carrier for iterative angular motion about a predetermined reference in a predetermined plane.

3. In a tissue slicer as defined in claim 2, means for expelling a quantity of said buffer medium intermediate said blade holder assembly and said reference slate responsive to movement of said tissue holder relative thereto.

4. In a tissue slicer for use in preparing tissue samples for medical research, including a base plate, a reciprocally movable blade assembly mounted thereon, a variable height reference plate adjacent said blade assembly defining an opening through said base plate intermediate said blade assembly and said reference plate a reservoir of buffer medium, and a tissue carrier cooperatively positioned to move a block of tissue relative to said blade assembly and said reference plate to create a slice of tissue having a predetermined thickness, the improvement comprising:

(a) means for reciprocally driving said blade assembly from eternally of said reservoir of buffer medium;

(b) means for iteratively urging said tissue carrier transversely of said blade assembly, detachably connected thereto by a reciprocating linkage extending above said medium and externally of said reservoir;

(c) means for positioning said tissue carrier for iterative angular motion about a predetermined reference in a predetermined plane; and, (d) means for expelling a quantity of said buffer medium intermediate said blade holder assembly and said reference plate responsive to movement of said tissue holder relative thereto comprising: a chamber formed within said tissue carrier, a first conduit extending from said reservoir to said chamber for providing fluid communication from said reservoir to said chamber for said buffer media, a second conduit extending from said chamber to a surface of said tissue chamber proximal said reference plate; a piston mounted for reciprocal movement within said chamber; resilient means for biasing said piston toward said second conduit; means for urging said piston to a charged position proximal said first conduit as said carrier traverses said blade assembly toward said reference plate; and means for releasing said piston from said charged position to expel fluids from said second conduit responsive to movement of said tissue carrier from said reference plate across said blade assembly.

5. In a tissue slicer as defined in claim 4 wherein said means for urging comprises a member extending from said chamber and connected to said piston, said member being of a length to engage an adjacent wall as said carrier moves within a predetermined distance thereof, and a latch pivotally mounted to frictionally engage said member under the influence of a resilient biasing member to hold said piston in said charged position.

6. In a tissue slicer as defined in claim 5, said means for releasing comprising a cam surface formed on said latch and a camming protrusion extending from said wall and adapted to engage said camming surface to urge said latch out of engagement with said extending member.

7. In a tissue slicer as defined in claim 2 where said means for positioning comprises an opening in said base plate for receiving said blade assembly and a pin extending therefrom through an aperture in said carrier such that said carrier is supported on and movable pivotally about said pin.

8. In a tissue slicer as defined in claim 7 wherein said means for iteratively urging comprises a lever affixed to said tissue carrier above said reservoir and means detachably affixed to said lever for urging said lever in a reciprocal arc about a vertical axis of said pin.

9. In a tissue slicer as defined in claim 1 wherein said means for iteratively urging comprises a lever affixed to said carrier above said reservoir and means detachably affixed to said lever for urging said lever in a reciprocating arc about a vertical axis passing through said carrier.

10. In a tissue slicer as defined in claim 1 wherein said means for reciprocating comprises:
   (a) a pin mounted to said blade assembly transversely of the direction of motion thereof;
   (b) an arm having a forked end slidably receiving said pin therein and a second end extending upwardly above said reservoir; and
   (c) means for reciprocatively moving said arm in an arc about a horizontal axis passing through said arm proximal said second end.

11. In a tissue slicer as defined in claim 10 wherein said means for iteratively urging comprises a lever affixed to said carrier above said reservoir and means detachably affixed to said lever for urging said lever in a reciprocating arc about a vertical axis passing through said carrier.

12. In a tissue slicer as defined in claim 11 wherein said means for reciprocally moving said arm comprises a first motor having a variable speed and an output shaft, said shaft carrying an eccentric pin in circular motion, and a linkage between said pin and said arm converting said circular motion to reciprocal motion.

13. An improvement to a biological tissue slicer for producing uniform tissue slices of a defined thickness from a tissue sample, usable in tissue culture experiments, having a base including a reference plate, variable in height relative to an upper surface of said base with a reference edge of said plate parallel an upwardly opening cavity, there being received within said cavity a blade mounted on a blade holder which moves reciprocally within a rectangular groove formed in said base within said cavity, wherein the improvement comprises:
   (a) a tissue holding carrier which moves reciprocally about a pivot point in a horizontal plane over said blade holder and said blade, said carrier having internal means for flushing said tissues slices past said blade into a collection trap beneath said base and said carrier; and
   (b) means detachably affixed to said blade holder for reciprocating said blade holder from a position above said blade holder, wherein said blade holder and said carrier are at least partially submerged in a buffer fluid within a reservoir and said reciprocating means are mounted externally of said reservoir.

14. An improved biological tissue slicer as defined in claim 13 wherein said means for flushing comprises a mechanical pump transversely mounted within said carrier, said pump actuated by reciprocal transverse movement of said carrier relative to said blade holder.

15. An improved biological tissue slicer as deemed in claim 14 wherein said carrier defines therein a transverse cylindrical chamber having a minor diameter opening proximal a wall which extends upward from a rear edge of said base, a major diameter opening distal said wall, and wherein a piston rod extends through said chamber, said rod having a piston coaxially mounted thereon, said piston having a diameter slightly less than said major diameter of said chamber.

16. An improved biological tissue slicer as defined in claim 15 wherein said carrier defines a first opening and first conduit which connects a lower surface of said carrier to an end of said chamber distal said wall, a second opening and second conduit connects an end of said chamber proximal said wall with the lower surface of said slicing block above said blade and said collection trap.

17. An improved biological tissue slicer as defined in claim 16 wherein said piston rod extends beyond said minor diameter, a portion of said rod extends beyond said minor diameter defining an extension, said extension having a smaller diameter than said rod, and further comprising a resilient spring mounted between said piston and said major diameter opening about said rod such that abutment of said extension with said wall forces said rod and piston against said spring, and means for releasably locking said rod and piston in a position compressing said spring.

18. An improved biological tissue slicer as defined in claim 16 wherein said means for locking comprises a trigger mechanism mounted to said carrier proximal said wall and resiliently biased against said extension to retaining said rod and piston within said chamber, and a pin cooperatively extending perpendicularly from said wall to urge said trigger mechanism from said rod as said carrier traverses said blade holder.

19. An improved biological tissue slicer as defined in claim 16 wherein said buffer fluid surrounding said carrier fills said first and second conduits and said chamber responsive to the movement of said piston.

20. An improved biological tissue slicer as defined in claim 13 wherein said means for reciprocating said blade is a vertical reciprocating arm which engages said blade holder at and end of said blade holder distal said blade, said vertical reciprocating arm connected to a first end of a horizontal axle transversely mounted in a wall which extends upward from the rear edge of said base, a vertical drive arm connected to a second end of said horizontal axle opposite said wall, said vertical drive arm connected at an end distal said second end to a eccentric drive wheel mounted to an shaft of an electric motor.

* * * * *

UNITED STATES PATENT AND TRADEMARK OFFICE
CERTIFICATE OF CORRECTION

PATENT NO. : 5,522,294
DATED : Jun. 4, 1996
INVENTOR(S) : Carlos Krumdieck

It is certified that error appears in the above-identified patent and that said Letters Patent is hereby corrected as shown below:

Column 6,
In claim 4, line 12, delete "eternally" and substitute --externally--.

Signed and Sealed this

Fourteenth Day of January, 1997

Attest:

BRUCE LEHMAN

Attesting Officer

Commissioner of Patents and Trademarks